(12) United States Patent
Kersey et al.

(10) Patent No.: US 12,163,891 B2
(45) Date of Patent: Dec. 10, 2024

(54) DIGITAL MIRROR DEVICE BASED CODE-DIVISION MULTIPLEXED RAMAN OPTICAL MAPPING SYSTEM FOR WIDE FIELD IMAGING

(71) Applicant: CytoVeris Inc., Farmington, CT (US)

(72) Inventors: Alan Kersey, South Glastonbury, CT (US); Rishikesh Pandey, Farmington, CT (US)

(73) Assignee: CytoVeris, Inc., Farmington, CT (US)

( * ) Notice: Subject to any disclaimer, the term of this patent is extended or adjusted under 35 U.S.C. 154(b) by 416 days.

(21) Appl. No.: 17/627,287

(22) PCT Filed: Jul. 16, 2020

(86) PCT No.: PCT/US2020/042415
§ 371 (c)(1),
(2) Date: Jan. 14, 2022

(87) PCT Pub. No.: WO2021/011823
PCT Pub. Date: Jan. 21, 2021

(65) Prior Publication Data
US 2022/0317046 A1    Oct. 6, 2022

Related U.S. Application Data

(63) Continuation-in-part of application No. PCT/US2020/016196, filed on Jan. 21, 2020.
(Continued)

(51) Int. Cl.
*G01N 21/65*    (2006.01)
*G02B 26/08*    (2006.01)
(Continued)

(52) U.S. Cl.
CPC ......... *G01N 21/65* (2013.01); *G02B 26/0833* (2013.01); *G02B 26/101* (2013.01);
(Continued)

(58) Field of Classification Search
CPC ........ G01J 3/021; G01J 3/0229; G01J 3/0289; G01J 3/06; G01J 3/08; G01J 3/44;
(Continued)

(56) References Cited

U.S. PATENT DOCUMENTS

2005/0084912 A1    4/2005    Poponin
2007/0263214 A1    11/2007   Fateley
(Continued)

OTHER PUBLICATIONS

Andreev, et al., pH-sensitive membrane peptides (pHLIPs) as a novel class of delivery agents, Mol. Membr. Biol., 27, pp. 341-352, 2010.
Antosh et al. "Enhancement of Radiation Effect on Cancer Cells by Gold-pHLIP", Proceedings of the National Academy of Sciences USA, Apr. 28, 2015, vol. 112, iss. 17, pp. 5372-5376.
(Continued)

*Primary Examiner* — Hina F Ayub
(74) *Attorney, Agent, or Firm* — Getz Balich LLC

(57) ABSTRACT

A system and method for mapping a tissue sample is provided. The system includes a light source, a scanner, a digital mirror device (DMD), a light detector, and an analyzer. The DMD has an array of micromirrors. The analyzer controls the light source, controls the scanner, controls the DMD to have on-state micromirrors aligned with a light beam, and other micromirrors in an off-state. The on-state micromirrors direct the light beam to a tissue sample. The analyzer assigns one or more location codes to the on-state micromirrors, controls the light detector to receive Raman light emitted from the tissue sample, correlates the location codes of the on-state micromirrors with light detector signals representative of the Raman emitted light, and produces a spatial map of the Raman emitted light.

21 Claims, 6 Drawing Sheets

Related U.S. Application Data

(60) Provisional application No. 62/874,694, filed on Jul. 16, 2019.

(51) Int. Cl.
*G02B 26/10* (2006.01)
*A61N 5/06* (2006.01)

(52) U.S. Cl.
CPC .... *A61N 5/062* (2013.01); *G01N 2201/06113* (2013.01); *G01N 2201/0636* (2013.01); *G01N 2201/1053* (2013.01)

(58) Field of Classification Search
CPC ............. G01N 2021/178; G01N 21/65; G01N 21/658; G01N 2201/06113; G01N 2201/0636; G01N 2201/1053; G01N 33/4833
See application file for complete search history.

(56) References Cited

U.S. PATENT DOCUMENTS

| | | | |
|---|---|---|---|
| 2010/0097604 A1* | 4/2010 | Duncan | G01J 3/021 356/326 |
| 2013/0296709 A1 | 11/2013 | Zuzak | |
| 2014/0253713 A1 | 9/2014 | Zhai | |
| 2017/0363741 A1 | 12/2017 | Send | |
| 2019/0129035 A1 | 5/2019 | Valouch | |
| 2020/0326238 A1* | 10/2020 | Akkus | G02B 26/0833 |
| 2022/0042916 A1* | 2/2022 | Notingher | G02B 21/16 |

OTHER PUBLICATIONS

Dahr et al. "A diffuse reflectance spectral imaging system for tumor margin assessment using custom annular photodiode arrays", Biomedical Optics Express, 3, (12), 2012.

Harmsen et al. "Cancer imaging using surface-enhanced resonance Raman scattering nanoparticles", Nat Protoc.; 11 (4); 664-87, 2016.

Ifa and Eberlin, "Ambient Ionization Mass Spectrometry for Cancer Diagnosis and Surgical Margin Evaluation", Clin Chem.; 62(1), 2016.

Korzeniowska et al., Intracellular pH-sensing using core/shell silica nanoparticles, J Biomed Nanotechnol., 10(7), pp. 1336-1345, 2014.

Mahadevan-Jansen et al. "Raman spectroscopy for the detection of cancers and precancers", J Biomed Opt;; 1 (1):31-70, 1996.

Matousek et al. "Noninvasive Raman spectroscopy of human tissue in vivo", Appl. Spectros. 60(7), 758-763, 2006.

Nguyen et al. "Fluorescence-guided surgery with live molecular navigation—a new cutting edge", Nat Rev Cancer, 13 (9), pp. 653-662, 2013.

Pence I. et al., "Clinical instrumentation and applications of Raman spectroscopy", Chem Soc Rev.; 45 (7):1958-1979, 2016.

Talari, A. et al., "Raman Spectroscopy of Biological Tissues", Applied Spectroscopy Reviews, 50:1, 46-111, 2015.

Tummers et al. "Real-time intraoperative detection of breast cancer using near-infrared fluorescence imaging and methylene blue", Eur J Surg Oncol. 40(7), 850-858, 2014.

Werakkoddy et al., Novel pH-Sensitive Cyclic Peptides, Scientific Reports, 6, 2016.

Wyatt et al. "Applications of pHLIP Technology for Cancer Imaging and Therapy", Trends in Biotechnology, Apr. 21, 2017, vol. 5, iss. 7, pp. 653-664.

Yaroslavsky. A, et al., "Delineating nonmelanoma skin cancer margins using terahertz and optical imaging", J of Biomedical Photonics & Eng., 3(1), 2017.

\* cited by examiner

DIGITAL MIRROR DEVICE BASED CODE-DIVISION MULTIPLEXED RAMAN OPTICAL MAPPING SYSTEM FOR WIDE FIELD IMAGING

This application is a national stage application of PCT/US2020/042415 filed Jul. 16, 2020, which claims priority to U.S. Patent Application No. 62/874,694 filed Jul. 16, 2019, which applications are incorporated by reference herein in their entirety. PCT/US2020/042415 is a continuation in part of PCT Application No. PCT/US2020/016196 filed Jan. 31, 2020, which is hereby incorporated by reference in its entirety.

BACKGROUND

For many decades the reference method for the diagnosis of cancer has been histopathological examination of tissues using conventional microscopy. This process is known as Surgical Pathology. In Surgical Pathology, tissue samples may be produced from surgical procedures (tumor resection), diagnostic biopsies or autopsies. These tissue samples are typically processed using a process that includes dissection, cutting precisely thin slices of the dissected tissue, fixation and staining of the tissue slices for contrast, and mounting of the same onto glass slides. The slides are typically then microscopically examined by a pathologist, and the pathologist's interpretation of the tissue results in the pathologic "read" of the sample.

Current surgical techniques to resect cancer tissue are limited by the lack of a precise method to determine the boundary between normal and cancerous cells/tissue, known as the "tumor margin," in real time during surgical procedures. The success of such surgical procedures relies on the experience and judgement of the surgeon to decide on how much tissue to remove around the tumor. As a result, surgeons often perform what is called "cavity shaving", which can result in the removal of excessive amounts of healthy tissue to improve the likelihood of removing all cancerous tissue. Conversely, in the event the entire tumor is not removed during the initial surgery, a patient may require follow-up surgery to remove residual cancer tissue. A follow-up surgery is very often traumatic to the cancer patient, adds stress to the patient, and often results in long-term detrimental effects on the patient outcome.

Advanced optical and other electromagnetic imaging approaches have been reported for the determination of tumor margin, such as: Fluorescence Imaging (e.g., See [1], [2]), Near Infrared Spectroscopy (e.g., See [3]), Raman Spectroscopy (e.g., See [4]-[8]), and Terahertz reflectivity (e.g., See [9]). Additionally, the use of Mass Spectrometry to profile tumor/normal tissue boundaries has been reported (e.g., See [10], [11]). In the latter methodology, a Mass Spectrometer coupled to a "pen" allows testing of tumor tissue by determination and differentiation of indicators of cancerous tissue, such as, for example, the metabolites produced by cancer cells compared to normal tissue.

It is known that all tumors exhibit an acidic microenvironment, largely due to the glycolytic metabolic processes exhibited by cancer cells. To maintain the rapid growth and proliferation exhibited by cancer cells, they have a higher need for energy which is, to a large degree, fulfilled by an increased dependence on alternate metabolic pathways. Under aerobic conditions, cancer cells metabolize glucose to lactic acid by a process generally called the Warburg effect (e.g., See [12]). Tumor tissue is also generally hypoxic (lacking in oxygen), has deficient blood perfusion, and has lower glucose levels (e.g., See [13]). Generally, this results in a microenvironment with pH of 6.4 to 6.8, whereas the surrounding normal tissue is close to neutral pH (7.2). The extracellular microenvironment acidity of cancer is associated with tumor progression and tumor metastasis (e.g., See [13], [14]).

Several approaches aiming to use this effect of low pH tumor microenvironment to allow targeted delivery of drugs to tumor sites have been explored, including pH sensing peptides (e.g., See [15], [16]), other peptides (e.g., See [17]), nanoparticles (e.g., See [18]), tumor cell-surface marker targeting (e.g., See [19]), etc. The pH sensing peptide, called pH (low) insertion peptide (pHLIP) is based on an amino acid sequence that reversibly folds and can insert across cell membranes in response to local intra-cellular low pH conditions. This folding of the pHLIP occurs due the increased hydrophobicity of the peptide in low pH environments. Consequently, the pHLIP peptide has proven itself as a versatile mechanism to target acidic tissue, and thus to image tumors via a variety of imaging modalities. The markers for imaging have included optical fluorescence markers and PET image contrast enhancement markers (e.g., See [20]). These approaches have also, in part, leveraged pH sensitive fluorescent dyes, such as Seminaphtharhodafluor (SNARF) dyes (e.g., See [21]), that change in their optical emission spectrum depending on the pH of the surrounding media/environment. Gold nanoparticles have been conveyed to tumors via pHLIPs (e.g., See [22]), but with the express intent of the enhancement of other imaging or therapeutic functions, e.g., enhancing radiation effects and increased cytotoxicity (e.g., See [23]). Additionally, pHLIP-coated hollow gold nanospheres have been used for enhancing the response of tumor cells to photodynamic therapy (e.g., See [24]).

SUMMARY

According to an aspect of the present disclosure, a system for mapping a tissue sample is provided. The system includes a light source configured to emit a beam of light, a scanner, a digital mirror device (DMD), at least one light detector, and an analyzer. The DMD has an orthogonal array of micromirrors, each micromirror selectively controllable to be in an on-state or an off-state. The analyzer is in communication with the light source, the scanner, the DMD, the at least one light detector, and a memory storing instructions, which instructions when executed cause the processor to: a) control the light source to produce the beam of light; b) control the scanner to scan the DMD with the beam of light; c) control the DMD to have a subset of micromirrors within the micromirror array in the on-state aligned with the beam of light scanning the DMD, and the micromirrors in the micromirror array not in the subset in the off-state, wherein at least some micromirrors in the subset of micromirrors in the on-state direct the beam of coherent light to a tissue sample location; d) assign one or more location codes to the subset of micromirrors in the on-state indicative of a location of the subset of micromirrors within the micromirror array; e) control the at least light detector to receive Raman light emitted from a tissue sample disposed in the tissue sample location, the Raman emitted light produced by the beam of light interrogation of the tissue sample, and to produce signals representative of the Raman emitted light; f) correlate the assigned one or more location codes of the subset of micromirrors with the signals representative of the Raman emitted light produced by at least one light detector; and g) produce a spatial map of the Raman emitted light using the signals representative of the Raman emitted light and the correlation between the assigned one or more location codes of the subset of micromirrors and the signals.

In any of the aspects or embodiments described above and herein, the light source may include one or more lasers, with each laser configured to emit a beam of light at a wavelength different from the other said lasers, and configured to cause said Raman emitted light to have a wavelength in the Raman silent region when interacting with at least one of an alkyne, nitrile, or azide moiety disposed with the tissue sample.

In any of the aspects or embodiments described above and herein, the scanner may be an X-Y Galvanometer scanner.

In any of the aspects or embodiments described above and herein, the instructions when executed may cause the processor to alter a resolution of the spatial map of the Raman emitted light, including controlling the DMD to increase the number of micromirrors in the subset of micromirrors within the micromirror array, or decreasing the number of micromirrors in the subset of micromirrors within the micromirror array.

In any of the aspects or embodiments described above and herein, the instructions when executed may cause the processor to control the DMD to increase the number of micromirrors in the subset of micromirrors within the micromirror array, and to cause the scanner to perform a first scan of the DMD at a lower said resolution, and to subsequently control the DMD to decrease the number of micromirrors in the subset of micromirrors within the micromirror array, and to cause the scanner to perform a second scan of at least a portion of the DMD at a higher said resolution.

In any of the aspects or embodiments described above and herein, the system may further include one or more narrow bandpass filters, the one or more narrow bandpass filters disposed to receive the Raman emitted light prior to the Raman emitted light being received by the at least one light detector, and the one or more narrow bandpass filters configured to only pass wavelengths of said emitted light in the Raman silent region.

In any of the aspects or embodiments described above and herein, the signals produced by the at least one light detector may be representative of the Raman emitted light wavelengths in the Raman silent region.

In any of the aspects or embodiments described above and herein, the spatial map of the Raman emitted light may represent Raman emitted light wavelengths in the Raman silent region.

In any of the aspects or embodiments described above and herein, the one or more assigned location codes may be a pseudorandom noise-like code.

In any of the aspects or embodiments described above and herein, the light source may be a laser that selectively produces a laser beam, and wherein the system may further include a line generating lens configured to convert the laser beam to a laser line having a width and a length, with the length extending a distance substantially greater than the width.

According to an aspect of the present disclosure, a method of mapping a tissue sample is provided. The method includes: a) providing a system having a light source configured to emit a beam of light, a scanner, a digital mirror device (DMD) having an orthogonal array of micromirrors, each micromirror selectively controllable to be in an on-state or an off-state, at least one light detector, and an analyzer in communication with the light source, the scanner, the DMD, and the at least one light detector; b) providing a tissue sample inoculated with a material containing pHLIPs conjugated with one or more Raman reporters (RR); c) scanning the DMD with a light beam produced by the light source, the scanning including using the scanner to move the light beam relative to the DMD; d) controlling the DMD to have a subset of micromirrors within the micromirror array in the on-state aligned with the light beam scanning the DMD, and the micromirrors in the micromirror array not in the subset in the off-state, wherein at least some of the micromirrors in the subset of micromirrors in the on-state are configured to direct the light beam to interrogate the tissue sample, wherein the interrogation produces Raman emitted light from the tissue sample; e) assigning one or more location codes to the subset of micromirrors in the on-state indicative of a location of the subset of micromirrors within the micromirror array; f) receiving the Raman emitted light from the tissue sample using the at least one light detector, and producing signals representative of the Raman emitted light; g) correlating the assigned one or more location codes of the subset of micromirrors with the signals representative of the Raman emitted light; and h) producing a spatial map of the Raman emitted light using the signals representative of the Raman emitted light and the correlation between the assigned one or more location codes of the subset of micromirrors and the signals.

In any of the aspects or embodiments described above and herein, the Raman reporters may be configured to produce a Raman spectrum in a Raman silent region when interrogated by the light beam.

In any of the aspects or embodiments described above and herein, the Raman reporters may be configured with at least one of an alkyne, nitrile, or azide moiety.

In any of the aspects or embodiments described above and herein, the method may further include filtering the Raman emitted light prior to the Raman emitted light being received by the at least one light detector, the filtering allowing only wavelengths of the Raman emitted light in the Raman silent region to pass through to the at least one detector.

In any of the aspects or embodiments described above and herein, the spatial map of the Raman emitted light may represent Raman emitted light wavelengths in the Raman silent region.

In any of the aspects or embodiments described above and herein, the controlling of the DMD may include selecting a resolution of the spatial map of the Raman emitted light, the subset of micromirrors within the micromirror array having a number of micromirrors, and the resolution based in part on the number of micromirrors within the subset of micromirrors.

In any of the aspects or embodiments described above and herein, the method may further include scanning the DMD a first time to produce the spatial map of Raman emitted light at a first said resolution, and scanning at least a portion of the DMD a second time to produce the spatial map of Raman emitted light at a second said resolution, which second said resolution is greater than the first said resolution.

In any of the aspects or embodiments described above and herein, the step of assigning one or more location codes to the subset of micromirrors in the on-state may include assigning a pseudorandom noise-like code.

In any of the aspects or embodiments described above and herein, the light source may be a laser that selectively produces a laser beam, and the method may further include converting the laser beam to a light beam line having a width and a length, with the length extending a distance substantially greater than the width, using a line generating lens.

In any of the aspects or embodiments described above and herein, the line generating lens may be configured to produce a light beam line in an orientation that aligns with rows in the orthogonal array of micromirrors, or in an orientation that aligns with columns in the orthogonal array of micromirrors.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

DETAILED DESCRIPTION

Aspects of the present disclosure include a novel and non-obvious system 18 and method for the detecting and mapping tissue samples for the presence or absence of cancer cells.

The present disclosure advantageously leverages Raman light scattering characteristics of certain materials for determining the presence or absence of cancerous cells/tissue. Raman light scattering refers to inelastic scattering in a material where there is an exchange of energy between the incident photons and the vibrational energy levels of the molecular bonds present in the material. All materials exhibit Raman scattering in response to incident light. The Raman spectrum for a given material is typically complex due to the variety of molecular bonds present within the material, and the material is identifiable based on the Raman spectrum. An exemplary Raman spectrum may include a number of different peaks at a certain wavelengths or "wavenumber" offsets from the incident light, which are uniquely characteristic of the material. Hence, the Raman spectrum of a particular material can be thought of as a "fingerprint" or "signature" of that particular material, and can be used for identification purposes. Human tissue has a particularly complex Raman spectrum, and the differences in the Raman spectrum associated with normal and diseased tissue can be subtle, but reproducible. The present disclosure provides a system 18 that facilitates collecting data that permits the identification of cancerous tissue using a Raman-tagging approach.

As indicated above, cancerous tumors exhibit an acidic micro-environment, largely due to the glycolytic metabolic processes exhibited by cancer cells. More specifically, cancer cells generally exist in an acidic microenvironment having a pH of 6.4 to 6.8, whereas normal tissue typically exists in a neutral pH environment; i.e., a pH close to 7.2. To maintain the rapid growth and proliferation associated with tumor progression and tumor metastasis, cancer cells have a greater need for energy which is to a large degree fulfilled by an increased dependence on alternate metabolic pathways. Under aerobic conditions, cancer cells metabolize glucose to lactic acid. Studies have shown that the pH in the vicinity of the plasma membrane of cancer cells is about 0.3-0.7 pH units lower than the bulk extracellular pH. Thus, cancer cells have been described as having a "crown of acidity" near their cell surfaces (e.g., See [21]). The bulk extracellular pH of tumor tissue generally correlates with perfusion, while the surface pH of cancer cells is expected to be less dependent on tumor tissue perfusion, and to be a predictive marker of tumor development and progression, since more aggressive tumor cells are more acidic.

Figure 1:
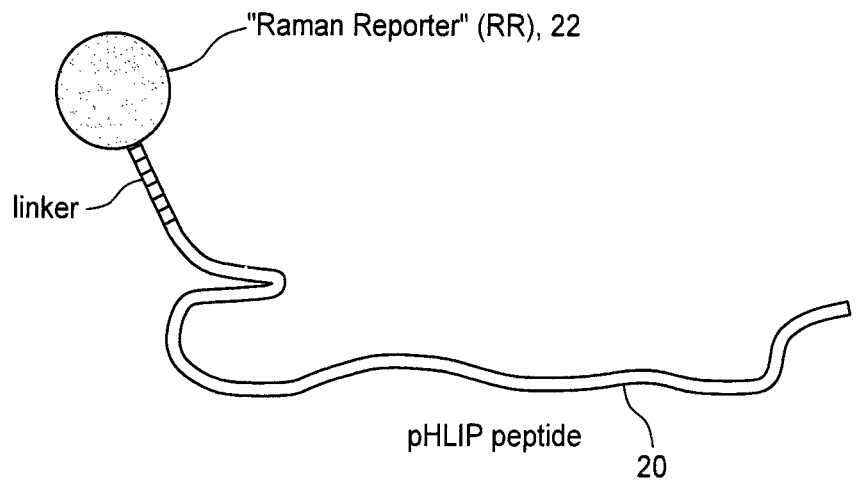
FIG. 1 illustrates an exemplary Raman Reporter.
Figure 2A:
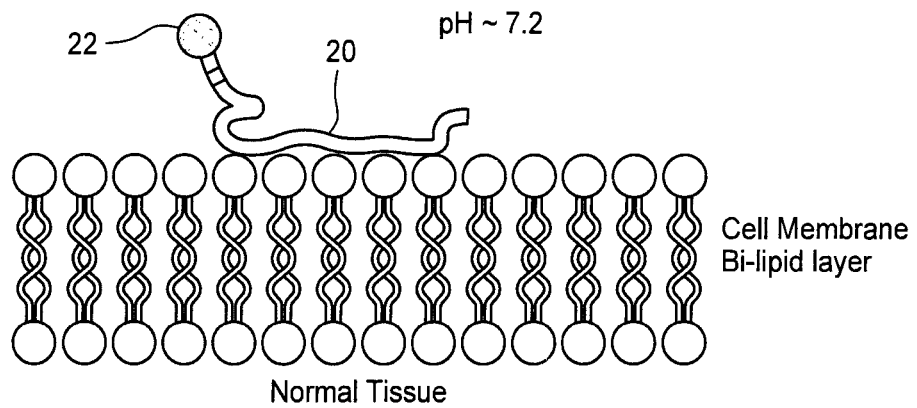
FIG. 2A diagrammatically illustrates an Alkyne-coated/adsorbed nanoparticle linked to a pHLIP peptide at a cell membrane for normal tissue.
Figure 2B:
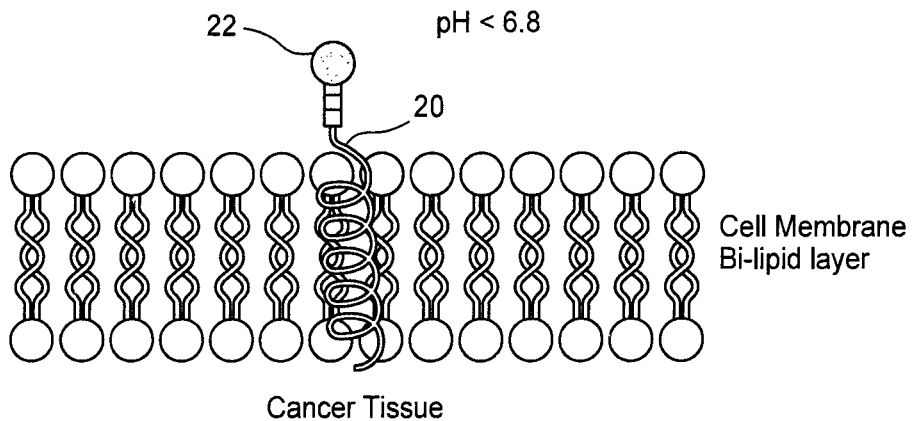
FIG. 2B diagrammatically illustrates an Alkyne-coated nanoparticle linked to a pHLIP peptide at a cell membrane for acidic tumor tissue.
Figure 3:
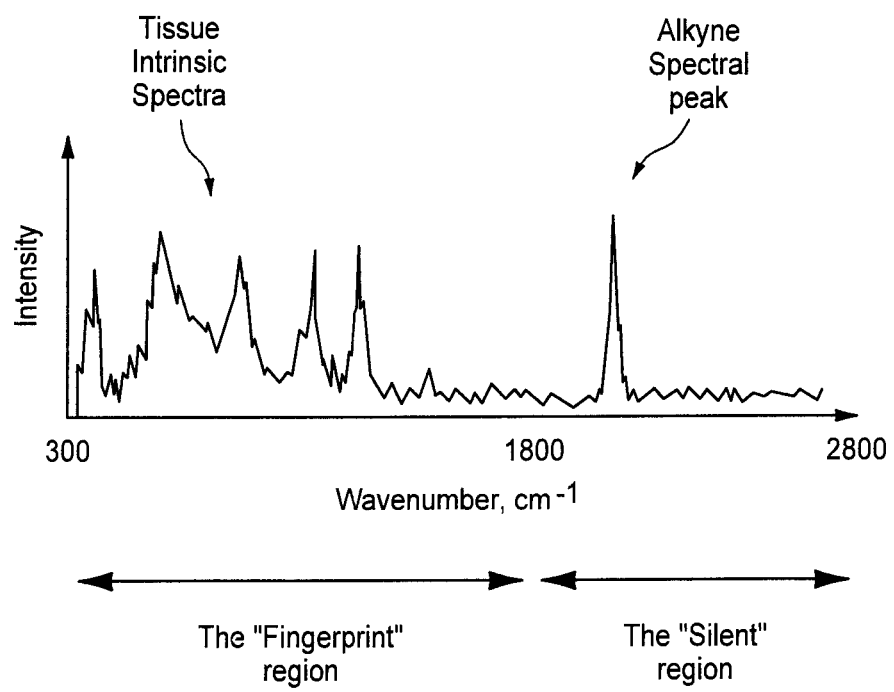
FIG. 3 is an intensity versus wavenumber graph diagrammatically illustrating Raman spectral identification in the silent region using Alkyne tagging.

Referring to FIGS. 1-3, some embodiments of the present disclosure utilize pH sensing peptides called pH (low) insertion peptides 20 ("pHLIPs") as a means of targeting/identifying cancer cells. The term "pHLIP" as used herein refers to its common application (i.e., generically referring to pH (low) insertion peptides) and not to any particular peptide produced by any particular source. Moreover, the present disclosure may utilize a variety of different pHLIPs 20 and is, therefore, not limited to any particular type of pHLIP. pHLIPs 20 are water-soluble membrane peptides that interact weakly with a cell membrane at neutral pH (e.g., see FIG. 2), but in a slightly acidic environment (pH<7.0) are capable of inserting into a cell membrane and forming a stable transmembrane alpha-helix (e.g., see FIG. 3); e.g., See [21], [25].

Figure 4:
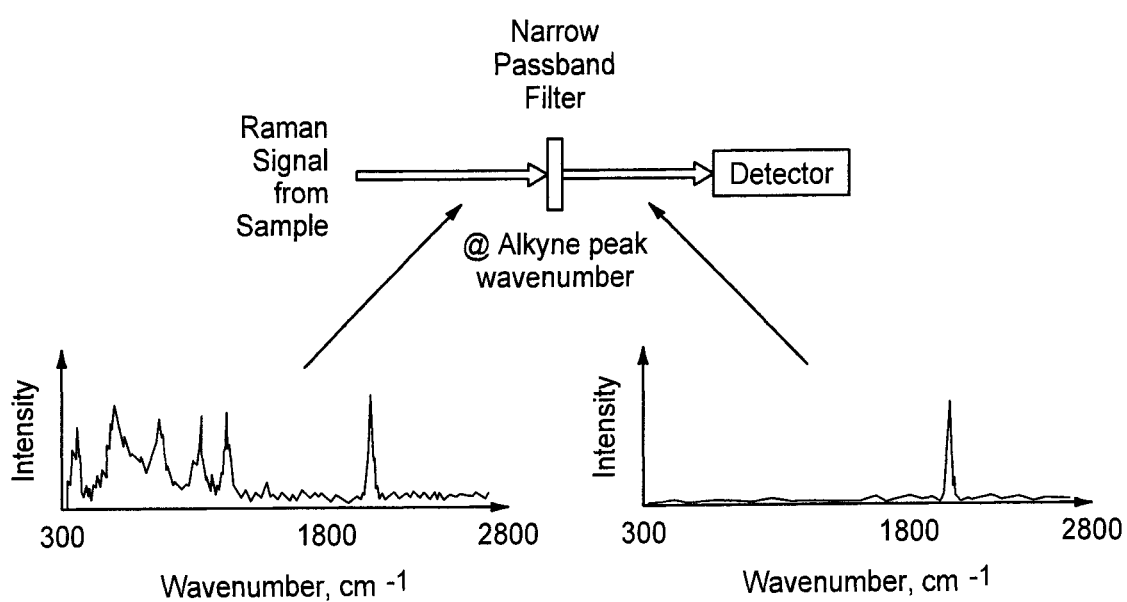
FIG. 4 is a pre-filtering intensity versus wavenumber graph and a post-filtering intensity versus wavenumber graph diagrammatically illustrating selective Alkyne response due to optical filtering.

Embodiments of the present disclosure utilize pHLIPs 20 to "tag" cancerous tissue with a substance (i.e., a Raman reporter 22, or "RR") having a Raman signature that is identifiable, and that can be distinguished from local tissue Raman signals. For example, an RR 22 may be conjugated with a pHLIP 20 (collectively referred to as a "RR-pHLIP") to create a vehicle for selectively delivering the RR 22 to the cancerous tissue, thereby facilitating identification of the location and geometry of the tissue cancerous mass. In some embodiments, a RR 22 may be anchored to a pHLIP 20 with a single or panel of antibodies to quantify the expression of biomarkers such as HER2, ER, EGFR, and CD44 in the cancerous region targeted by the pHLIP 20. The expression/absence of biomarker(s) helps in classifying certain tissue types that are otherwise difficult to conclude from haemotoxylin and eosin ("H&E") staining-based morphological features. Referring to FIGS. 3 and 4, in some embodiments of the present disclosure, RRs 22 may be configured to produce a Raman spectrum in the "Raman silent region" where the Raman spectra of endogenous biospecies (e.g., non-cancerous and/or cancerous tissue intrinsic Raman spectra, including Raman spectra associated with tissue calcifications, etc.) are typically negligible. The present disclosure is not limited using RRs 22 configured to produce Raman spectra in the Raman silent region. An example of an RR 22 that is configured to produce Raman spectra in the Raman silent region is one that includes an alkyne, a nitrile, or an azide moiety, or the like, or a compound containing such molecular sub-groups, such as EdU (5-ethynyl-2'-deoxyuridine) (e.g., see [0026]), bonded to the surface of a nanoparticle to produce a Raman spectrum in the Raman silent region. Alternatively, an alkyne, nitrile, or azide (or similar) moiety may be "linked" to a pHLIP 20, thereby obviating the need for an independent RR 22. The term "linked" as used here refers to any mechanism that permits the moiety or compound that produces a Raman spectrum in the Raman silent region to be connected with, or be incorporated as a part of, a pHLIP 20. As a non-limiting example, and as described below, pHLIPs 20 may be synthesized with amino acids that contain alkyne or other functional groups built into the pHLIP chain. Alkyne (a carbon-carbon triple bond) exhibits strong and characteristic peaks in the Raman silent region (typically about 1800 $cm^{-1}$ to 2800 $cm^{-1}$). The depiction within FIG. 3 of tissue intrinsic Raman spectra within both the fingerprint and silent regions, and Alkyne spectral peak within the silent region illustrates well the significance of utilizing a RR 22 that produces a Raman spectrum within the silent region. In the silent region the tissue intrinsic Raman spectra is negligible relative to the Alkyne spectral peak, and consequently the identification of the RR 22 Raman spectrum is significantly enhanced.

In some alternative embodiments, in addition to carbon-carbon or carbon-nitrogen triple bonds, the C—H frequency of Alkyne/Nitrile may be used to report the presence and concentration of an Alkyne/Nitrile moiety. In some embodiments, Polyethylene glycol (PEG) containing an Alkyne moiety could be coated or otherwise attached to a nanometallic surface. The Alkyne moiety can either be a known molecular entity or a conjugated system either with a fluorophore, DNA or any other molecular species which can act as a secondary/surrogate marker.

In some embodiments of the present disclosure, an RR 22 may be configured with a Surface Enhanced Raman Spectroscopic ("SERS") substrate material with one or more Raman dye molecules attached/adsorbed to the substrate surface. This substrate material is typically a metallic material, and most often takes the form of a nanoparticle or nanostructure including nanostars. Upon light interrogation, a SERS substrate material provides Raman spectra response that is greatly enhanced (e.g., See [0024]-[0029]). SERS modified RRs 22 according to the present disclosure provide a Raman spectra response greatly enhanced relative to a Raman spectra response produced by intrinsic biospecies. The enhancement effects of a Raman signal is generally attributed due to the excitation of localized surface plasmons, or chemical charge transfer, or some combination thereof. The SERS effect has been demonstrated in metals such as gold (Au) and silver (Ag), as well as platinum (Pt), ruthenium (Ru), palladium (Pd), iron (Fe), cobalt (Co), nickel (Ni), lithium (Li), sodium (Na), potassium (K), rubidium (Rb), copper (Cu), and the like. However, the SERS enhancement effect is much stronger for particles comprising a plasmonic material (e.g., noble metal, such as Au, Ag, etc.), or alkali metals (e.g., Li, Na, K, Rb, etc.), or certain base metals (e.g., Cu, etc.), or combinations or variants thereof. In some instances, an RR 22 may include novel materials such as graphene or other 2D materials that may form the basis of a SERS substrate.

Figure 5:
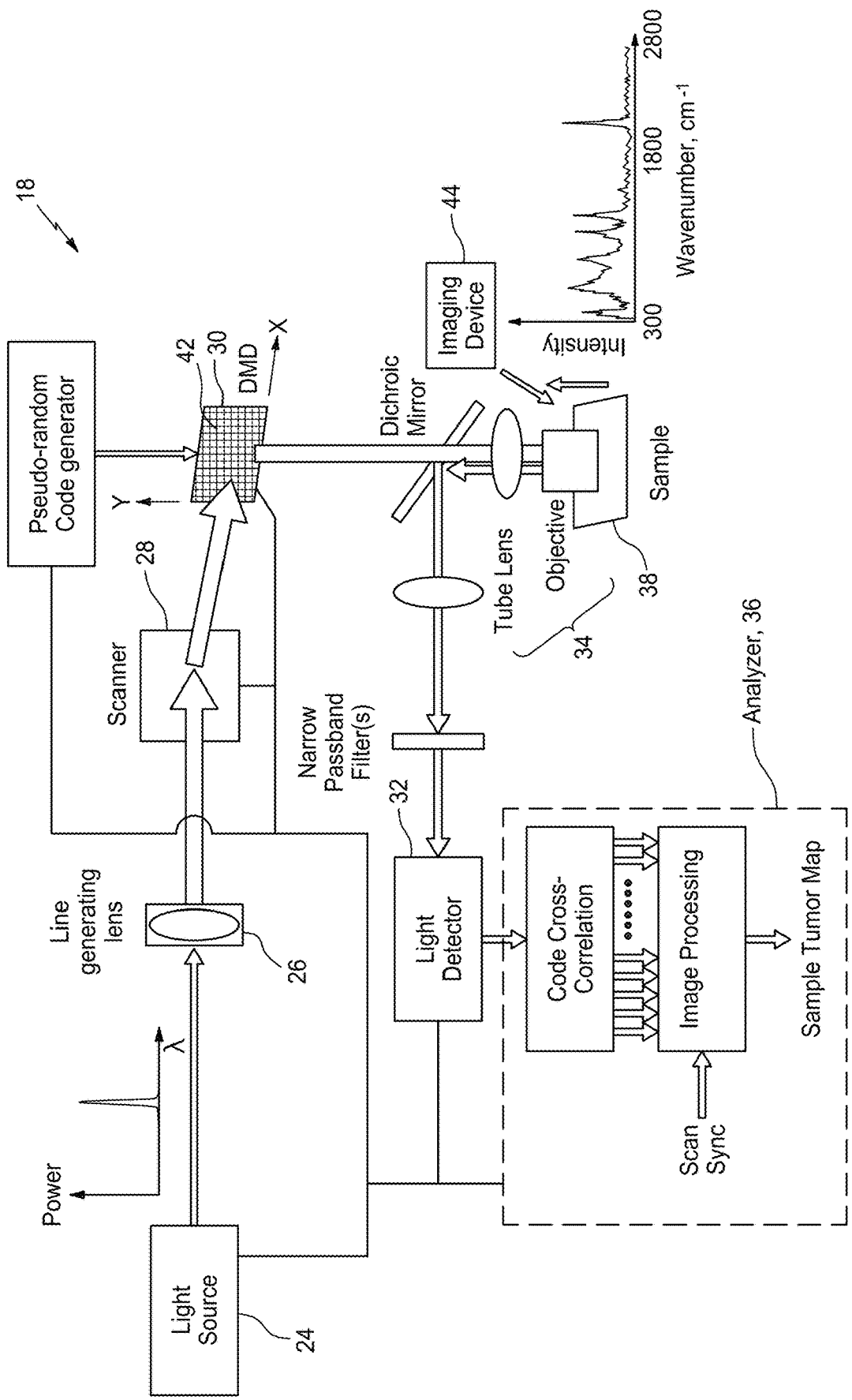
FIG. 5 schematically illustrates an exemplary apparatus for optically mapping a surface of a tissue sample.

A diagrammatic illustration of a present disclosure system 18 exemplary embodiment is shown in FIG. 5. The system embodiments include at least one light source 24, a scanner 28, a digital mirror device (DMD) 30, at least one light detector 32, optics 34, and an analyzer 36. In some embodiments, the system may include a line generating lens 26. As will be described herein, the configuration of these components may vary in different system 18 embodiments. The system 18 embodiment description provided herein may refer to various different system components as independent components. The present disclosure is not limited to specific descriptions provided herein. For example in alternative embodiments, system components may be combined, or arranged in a different manner than that shown in the Figures, and still be within the scope of the present disclosure.

The light source 24 is configured to emit a beam of coherent light. The light beam generated directly from the laser(s) may have a variety of beam geometric configurations (e.g., circular, rectangular, square, etc.). As will be explained below, the light beam from a laser may also be shaped "downstream" of the laser exit; e.g., a line generating lens is described below that transforms a light beam into a line. Optical devices other than a line generating lens may be used to transform a light beam into alternative geometric configurations; e.g., square, rectangular, elliptical, etc. An example of an acceptable coherent light source 24 is a laser. A variety of different lasers may be used within the system 18, and the present disclosure is not therefore limited to using any particular laser. The present disclosure may utilize coherent light at a variety of different wavelengths, and the light source 24 is therefore not limited to coherent light at any particular wavelength or wavelength band. Light from the light source 24 may be transferred within the system 18 and to and from the subject tissue via optical fibers or other light conduit.

The line generating lens 26 is configured to accept the light beam from the light source 24 (e.g., circular shape) and convert it to a straight, uniform line (i.e., a "light beam line"). In some embodiments, the laser generating lens 26 may produce a light beam line having a substantially even optical power distribution. The present disclosure is not limited, however, to any particular line generating lens 26 configuration. Non-limiting examples of line generating lenses include a cylindrical lens, a Powell lens, and the like. As stated above, in some embodiments an optical device other than a line generating lens may be used to transform a light beam into alternative geometric configurations; e.g., square, rectangular, elliptical, etc.

The scanner 28 is in communication with the analyzer 36 and can be controlled based on instructions stored within the analyzer 36. The scanner 28 is selectively controllable to direct the laser line exiting the line generating lens 26 to various positions on the DMD 30. In some embodiments, the scanner may be operable to direct the laser to sweep along an X-axis; e.g., to sweep a laser line to impinge on successive columns within the DMD 30 micromirror array. In some embodiments, the scanner may be operable to direct the laser to sweep along a Y-axis; e.g., to sweep a laser line to impinge on successive rows within the DMD 30 micromirror array. In some embodiments, the scanner may be operable to direct the laser to move along both the X-axis and the Y-axis of the DMD 30 micromirror array. As will be discussed below, when the micromirrors in the DMD array are in their on-state, the laser line incident on the DMD 30 is reflected onto a sample (at a tissue sample location) under evaluation (e.g., a tissue sample). If the micromirror elements of the DMD 30 are in their off-state, the laser line is directed away from the tissue sample. As will be discussed below, in some embodiments, the system 18 may be configured to scan a tissue sample 38 at a first lower spatial resolution, and subsequently at a second higher spatial resolution; e.g., scan a portion or all of the tissue sample 38 at the first lower resolution to identify areas of interest, and subsequently scan any identified areas of interest at the second higher resolution. In these embodiments and others, the scanner 28 is controllable to direct laser light to only the identified areas of interest; e.g., return to the area of interest to permit the second higher resolution scan. In some embodiments, the scanner 28 and DMD 30 are collectively configured such that a laser line impinging the DMD 30 is in alignment with one or more columns within the DMD 30 micromirror array. In some embodiments, the scanner 28 and DMD 30 are collectively configured such that a laser line impinging the DMD 30 is in alignment with one or more rows within the DMD 30 micromirror array. An example of a scanner 28 that may be used with the present disclosure is a Galvanometer scanner (sometimes referred to as a "Galvo" scanner).

The DMD 30 (sometimes referred to as a digital micromirror device) typically includes several hundred thousand (and in some instances substantially more) microscopic mirrors (sometimes referred to as "pixels" or "mirror-pixels") arranged in an orthogonal array. The term "orthogonal" as used herein refers to a DMD having an array with rows and columns that are substantially perpendicular (i.e., orthogonal) to one another. Each micromirror can controlled to pivot between an "on-state" and an "off-state". In an on-state, each micromirror is positioned to reflect light in a first direction; e.g., to deflect the light in a direction desired to permit interrogation of the tissue sample 38 by the deflected light (i.e., to a tissue sample location). In an off-state, each micromirror is positioned to reflect light in a second direction, different from the first direction; e.g., to deflect the light in a direction where it does not participate in the interrogation of the tissue sample 38. The DMD 30 is in communication with and can be controlled by instructions stored within the analyzer 36. The present disclosure can use any DMD 30 operable to satisfy the system 18 operations as described herein, and is not therefore limited to any particular DMD 30.

The optics 34 include one or more filters, mirrors, and lenses disposed to process/direct light within the system 18 that will be used to interrogate a tissue sample 38, and light emitted from the tissue sample 38 as a result of the interrogation. The optics 34 may include a dichroic mirror positioned and configured to permit interrogation light to pass through and onward to a tissue sample 38 and to reflect light emitted from the tissue sample 38 toward the light detector 32 for collection by the light detector 32. The optics 34 may include one or more tube lenses for conditioning light directed to and/or emitted from the tissue sample 38. The optics 34 may include one or more narrow bandpass filters configured to process only light at wavelengths associated with defined Raman spectra peaks. For example, in the case of an RR 22 that is configured to produce a Raman spectral signature in the silent region, the narrow bypass filter may be configured to pass only those wavelengths associated with the silent region (e.g., about 1800 $cm^{-1}$ to 2800 $cm^{-1}$). The optics 34 may include one or more objective lenses. The optics 34 may include fiber optic links operable to act as a light conduit within the system 18.

The at least one light detector 32 is configured to receive light (e.g., Raman spectra) emitted from the interrogated tissue via the optics 34 and produce signals representative thereof. The signals produced by the light detector 32 are transferred to analyzer 36. Non-limiting examples of light detectors 32 include light sensors that convert light energy into an electrical signal such as a simple photodiode, or other optical detectors of the type known in the art, such as a CCD array or a CMOS camera. Preferably, the light detector 32 is a large area light detector having sufficient area to capture light emitted from the entirety of the tissue sample 38 being analyzed, or alternatively a large area detector may be formed using a CCD detector array and summing all of the pixels to give total optical power/signal.

The analyzer 36 is in communication with other components within the system 18, such as the light source 24, the scanner 28, the DMD 30, and the light detector 32 to control the functions of the respective components; e.g., communicate signals to and/or from the respective components to perform the functions described herein. The analyzer 36 may include any type of computing device, computational circuit, processor(s), CPU, computer, or the like capable of executing a series of instructions that are stored in memory. The instructions may include an operating system 18, and/or executable software modules such as program files, system data, buffers, drivers, utilities, and the like. The executable instructions may apply to any functionality described herein to enable the system 18 to accomplish the same algorithmically and/or coordination of system 18 components. The analyzer 36 may include a single memory device or a plurality of memory devices. The present disclosure is not limited to any particular type of non-transitory memory device, and may include read-only memory, random access memory, volatile memory, non-volatile memory, static memory, dynamic memory, flash memory, cache memory, and/or any device that stores digital information. The analyzer 36 may include, or may be in communication with, an input device that enables a user to enter data and/or instructions, and may include, or be in communication with, an output device configured, for example to display information (e.g., a visual display or a printer), or to transfer data, etc. Communications between the analyzer 36 and other system 18 components (e.g., the light source 24, light detector 32, etc.) may be via a hardwire connection or via a wireless connection.

Embodiments of the present system 18 are configured to interrogate regions of a tissue sample 38 with light, collect light emitted from the sample regions as a result of the interrogation, and correlate the sample emitted light to the specific region being interrogated to produce a spatial map ("image") of the emitted light. The location of the tissue region being interrogated can be spatially defined using the orthogonal array of micromirrors 42. In fact, the orthogonal array of the DMD micromirrors 42 and the ability to control the DMD 30 to sequentially place some (e.g., a first subset of) micromirrors 42 in an on-state and the remaining micromirrors (e.g., a second subset) in an off-state, provide an advantageous means of spatially locating all of the regions of the tissue sample 38 as they are interrogated. The operation of the scanner 28 and the DMD 30 are coordinated such that a subset of on-state micromirrors 42 impinged with light from the scanner 28 directs the light to a region of the tissue sample 38, and the process is sequentially repeated until the desired region of the sample has been completely interrogated; e.g., place a subset of micromirrors in the on-state, with remaining micromirrors in the off-state (while the on-state micromirrors are impinged with light), and then place a new subset of micromirrors in the on-state and place the remaining micromirrors (including the micromirrors previously in the on-state) in the off-state (while the on-state micromirrors are impinged with light), and so on until all of the desired region of the tissue sample has been interrogated. Light emitted from the sample 38 as a result of the interrogation is collected substantially synchronously with the light interrogation, and is correlated with the spatial location of the interrogated tissue sample 38. A portion or all of the sample 38 can be interrogated in this manner, the emitted light correlated to the position of the respective sample 38 region, and a spatial map ("image") of the emitted light produced. The on-state micromirrors 42 direct the interrogating light to a portion of the tissue sample 38 and the location of the respective tissue sample 38 portion is determinable using the orthogonal location of the on-state micromirrors 42 (as will be described below, the specific relative location of each on-state micromirror 42 may be coded to facilitate correlating location). The light emitted from the sample 38 as a result of the interrogation is collected substantially synchronously with the light interrogation, and passed to the light detector 32. In some embodiments, prior to reaching the light detector 32, the emitted light is passed through one or more narrow passband filters. The narrow passband filter(s) are configured to allow only those wavelengths of light associated with Raman spectra from the silent region (the "silent region light") to pass through to the light detector 32. The light detector 32 produces signals representative of the silent region light and communicates those signals to the analyzer 36. The analyzer 36 correlates the signals from the light detector 32 with the spatial information from or based on the DMD 30, and produces a spatially correct map (e.g., an image) of the silent region light emitted from the tissue sample 38. The silent region light map provides useful information relating to the presence or absence of cancerous cells, and therefore useful information regarding tumor margin. To be clear, the present disclosure is not limited to producing a spatial map of emitted light of only those wavelengths in the Raman silent region. Emitted light in the Raman silent region is advantageous because it is distinctive, but is not required. In some embodiments, the spatial map of emitted map may be based on any Raman spectrum that is distinguishable from Raman spectra produced by intrinsic biospecies (e.g., healthy tissue) or the like. As stated above, in some embodiments RRs 22 may be SERS modified to provide a Raman spectra response that is greatly enhanced relative to a Raman spectra response produced by intrinsic biospecies. In these instances, the Raman spectra response—which is not necessarily in the Raman silent region—may be readily distinguishable and can be used to produce a spatial map of emitted light indicative of the presence of cancerous tissue.

To illustrate further, the following non-limiting detailed example of the present disclosure system 18 operation is provided. A tissue sample/specimen suspected of being cancerous is inoculated with a material containing pHLIPs 20. As described above, the pHLIPs 20 are either conjugated with a Raman reporter 22 (RR), or are configured themselves to function as a RR 22 (collectively referred to hereinafter as "RR-pHLIPs"). In preferred embodiments, the RR-pHLIPs are configured to produce a Raman signature in the silent region (e.g., see FIGS. 3 and 4), and may in some instances be SERS modified to provide a Raman spectra response greatly enhanced relative to a Raman spectra response produced by intrinsic biospecies. The aforesaid RR-pHLIPs may be conveyed to the suspect tissue using several different techniques, such as by intravenous administration of a material containing the RR-pHLIPs, or by topically applying a material containing the RR-pHLIPs over suspected tumor tissue surface, etc. The present disclosure is not limited to these exemplary application techniques. A topical application technique may, for example, be suitable in applications such as in-vivo bladder cancer detection, or ex-vivo excised tumor specimen profiling, etc. In the blood stream, the RR-pHLIPs react to the local pH in a tumor microenvironment. The cell binding mechanism or cell membrane penetration mechanism of the pHLIPs 20 immobilizes and localizes the RR-pHLIPs to the cancer cell surface, as illustrated in FIGS. 2A and 2B. The RR-pHLIPs that do not bind to cancerous cells are cleared through the system 18 in a matter of several hours. In the case where a material containing the RR-pHLIPs is administered by topical delivery, the excess, unbound complex could be washed off in a simple multiple cycle washing procedure.

After material containing RR-pHLIPs is conveyed to tissue suspected of being cancerous, and any unbound RR-pHLIPs have cleared or been washed from the region, the tissue region is interrogated with light produced by the light source. In those system embodiments that include a line generating lens 26, the light beam produced by the light source 24 is converted into a line (e.g., a "light beam line") having a width and a length, with the length extending a distance substantially greater than the width. In some embodiments, the line generating lens 26 may be configured to produce a vertically extending line (i.e., the length of the line extending along the Y-axis). In these embodiments, the light beam line directed to the DMD 30 by the scanner 28 would be substantially parallel to the Y-axis micromirror columns of the micromirror array. In some embodiments, the line generating lens 26 may be configured to produce a horizontally extending line (i.e., the length of the line extending along the X-axis). In these embodiments, the light beam line directed to the DMD 30 by the scanner 28 would be substantially parallel to the X-axis micromirror rows of the micromirror array. In those embodiments that include a line generating lens 26, the scanner 28 and the DMD 30 are preferably configured such that the light beam line directed to the DMD 30 from the scanner 28 engages one or more columns of the DMD 30 array (e.g., when the line generating lens produces a vertical light beam line), or configured such that the light beam line directed to the DMD 30 from the scanner 28 engages one or more rows of the DMD 30 (e.g., when the line generating lens produces a horizontal light beam line). The micromirrors 42 engaged by the light beam line are controlled to be in an on-state. The light beam line engaging the micromirrors 42 in the on-state exits the DMD 30, passes through the dichroic mirror, and is directed to a portion of the tissue sample 38.

Figure 6:
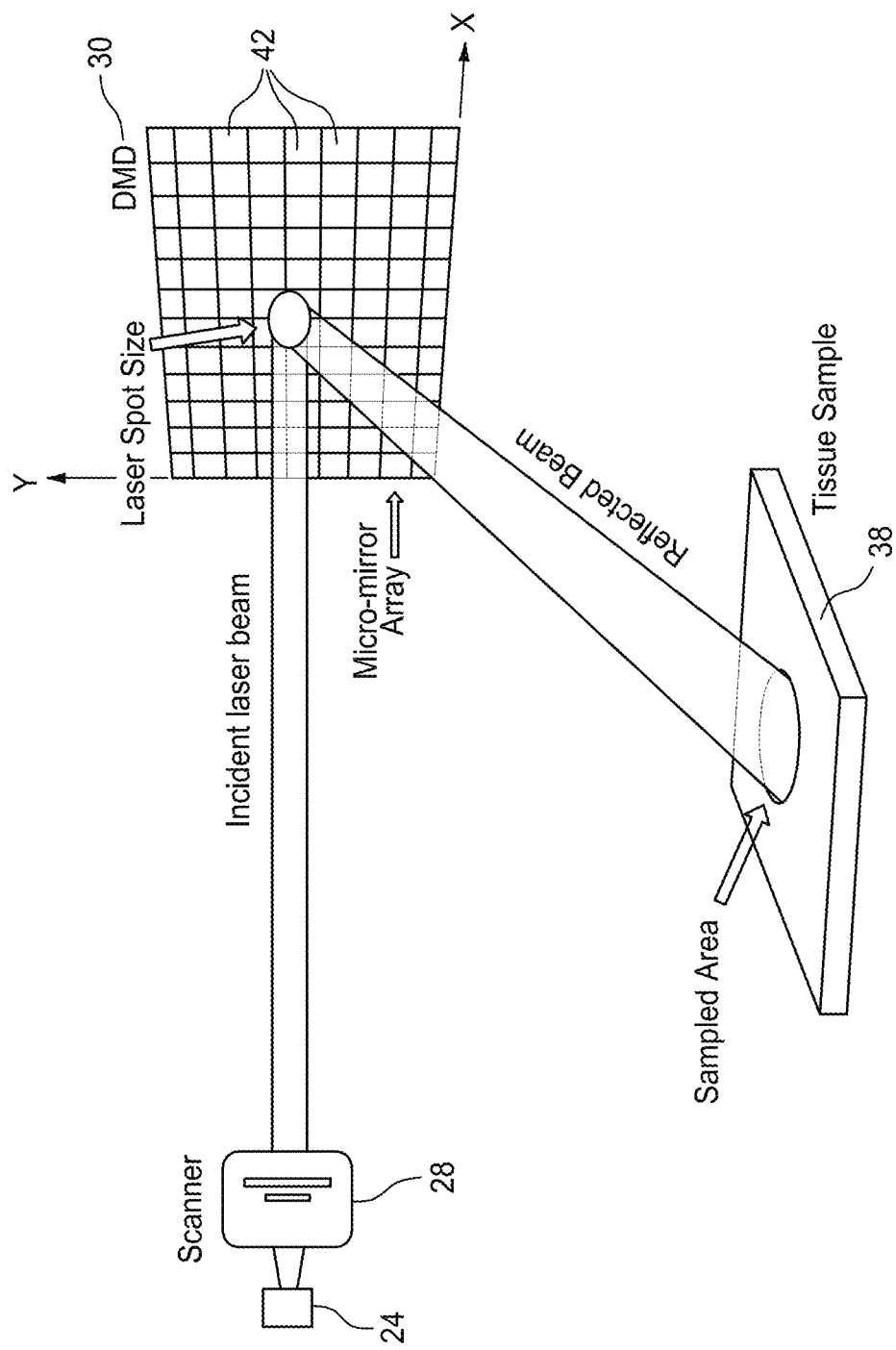
FIG. 6 is a diagrammatic representation of a portion of a present disclosure system embodiment.
Figure 7:
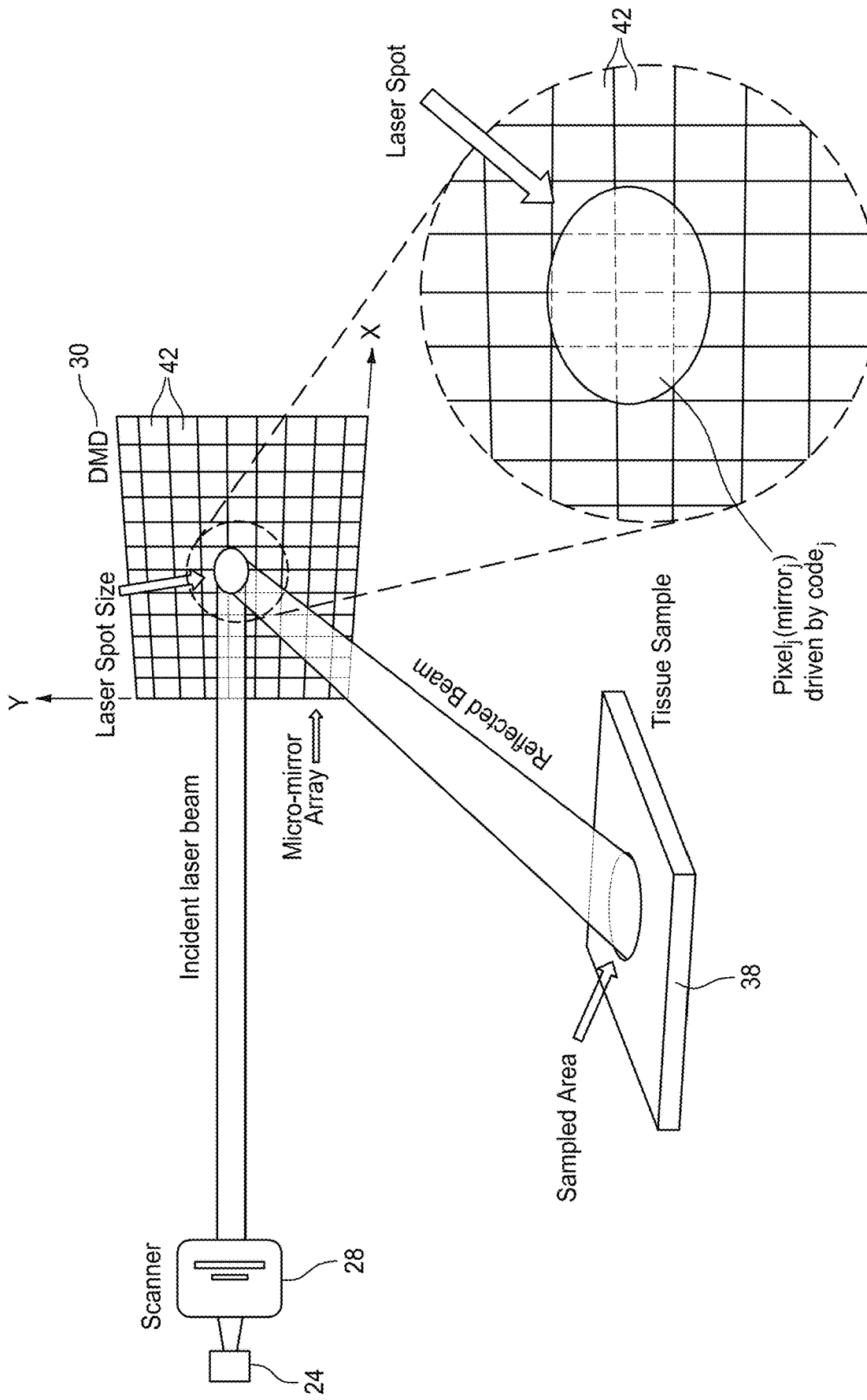
FIG. 7 is a diagrammatic representation of a portion of a present disclosure system embodiment shown in FIG. 6, including an enlarged view of a light beam incident to a digital mirror device.

As indicated above, some embodiments the present disclosure do not utilize a line generating lens, and consequently do not produce a light beam line interacting with the array micromirrors 42. For reasons explained herein, such embodiments may be advantageous in some applications, but are not required. Referring to FIGS. 6 and 7, in some embodiments the light beam produced by the light source 24 (in its original geometric form or in a geometric form other than a line) may be directed to the DMD 30 by the scanner 28. In these embodiments, the scanner 28 may be configured to raster (i.e., in the X-Y plane) the light beam across a portion or all of the DMD array, with the DMD switching micromirrors impinged upon by the light beam into an on-state, and the remaining micromirrors 42 into an off-state.

The tissue sample 38 portion now being interrogated by the light will produce emitted light (e.g., Raman spectra, fluorescent emissions, etc.). The emitted light, in turn is directed back towards the dichroic mirror, which directs the emitted light to the narrow passband filter(s). The narrow passband filter(s) are configured to allow only those wavelengths of emitted light associated with Raman spectra from the silent region (the "silent region light"). If no cancerous tissue is present within the tissue being interrogated (i.e., no RR-pHLIPs bound to tissue cells are present), none of the emitted light will include silent region light. Silent region light that is emitted, however, will pass through the narrow passband filter(s) and will subsequently be incident to the light detector 32. In those embodiments that do not include a narrow passband filter(s) (e.g., those embodiments wherein the RRs 22 produce Raman spectra that is distinguishable from the Raman spectra produced by intrinsic biospecies—not indicative of cancerous tissue), the dichroic mirror may direct the emitted light directly to the light detector 28. The light detector 32 produces signals representative of the emitted light and provides those signals to the analyzer 36 for analysis of the signals.

As stated above, the operation of the scanner 28 and the DMD 30 is coordinated so that the light beam line (or light beam) directed to the DMD 30 from the scanner 28 traverses ("scans") the DMD 30. The micromirrors 42 engaged by the light beam line (or light beam) are controlled to be in the on-state and the remaining micromirrors are controlled to be in the off-state. As the traversing light beam line (or light beam) engages new micromirrors 42, those micromirrors 42 are controlled to be in the on-state and the remaining micromirrors are controlled to be in the off-state. The aforesaid sequential scanning of the DMD 30 permits the tissue sample 38 to be sequentially interrogated by the light until all of the desired region of the sample tissue 38 has been interrogated. It should be noted that the light beam line (or light beam) may engage off-state micromirrors (e.g., the light beam may be incident to an array area that is greater than the array area taken up by the on-state micromirrors). As stated above, the off-state micromirrors are configured to deflect the light in a direction where it does not participate in the interrogation of the tissue sample 38.

The number of micromirrors 42 disposed on-state and the manner in which they are disposed in the on-state as the light beam line (or light beam) scans the DMD 30 can be varied to suit different modes of operation. As stated above in those embodiments that include a line generating lens 26, the operation of the scanner 28 and the DMD may be coordinated such that the light impinging the DMD may be oriented vertically to coincide with one or more array columns in an on-state, or may be oriented horizontally to coincide with one or more array rows in an on-state. In these embodiments, all or less than all of the micromirrors 42 in the column(s)/row(s) may be in an on-state. The remaining micromirrors 42 are in the off-state. As the light beam light traverses the array, columns or rows of micromirrors 42 are sequentially changed from on-state to off-state, and vice versa, until a selected region or all of the DMD has been impinged with light (and therefore a selected portion or all of the tissue sample has been interrogated). The present disclosure in not limited to any particular scanning algorithm. As described above, the scanning process may sequentially scan rows of the array, or sequentially scan columns of the array, or sequentially scan areas of the array. In those embodiments that do not include a line generating lens (e.g., see FIGS. 6 and 7), the area of the light beam produced by the light source (which may be expanded optically) may impinge on a region of the array that includes micromirrors 42 within a plurality of columns and rows (e.g., an area—a "macro-pixel"—that encompasses a 5×5 micromirror portion of the array). In these embodiments, the scanner 28 may be configured to raster the light beam across a portion or all of the DMD array, with the DMD switching micromirrors impinged upon by the light beam into an on-state, and the remaining micromirrors 42 into an off-state. The sequential changing of the micromirrors from on-state to off-state, and vice versa is as described above.

As stated above, the signals from the light detector 32 representative of light emitted from the tissue sample 38 are correlated with spatial information from or based on the DMD 30. In some embodiments, the aforesaid correlation may include assigning a code or other indicia to each on-state micromirror 42 that provides information regarding the location of that specific micromirror 42 within the DMD 30 array. The analyzer 36 is configured to use the assigned code to cross-correlate the substantially synchronously received emitted light signals and thereby spatially locate the emitted light signals to produce a spatially correct map (e.g., an image) of the silent region light emitted from the tissue sample 38.

An example of a coding technique that may be used to correlate the location of the on-state micromirrors 42 within the DMD 30 array (and therefore the location of the tissue sample 38 being interrogated) with the emitted light signals resulting from the interrogation is one that utilizes a pseudorandom noise-like code with high orthogonality between codes (e.g., a Gold code). The functionality of the analyzer 36 controlling the DMD 30 may produce the pseudorandom noise-like code as an identifier of the DMD micromirrors 42 disposed on-state, and the same pseudorandom noise-like code may be subsequently cross-correlated by the analyzer 36 to spatially locate the emitted light signals to produce the spatial map (e.g., image) of the silent region light emitted from the tissue sample 38. The pseudorandom noise-like code can be configured to provide an identifier to each micromirror 42 in the on-state so that the emitted light collected substantially synchronously can be attributed to the respective micromirror, and therefore the respective region of the tissue sample. For example, the pseudorandom noise-like code can be configured to permit the on-state micromirrors 42 to be modulated, which modulation enables each on-state micromirror 42 to be identified individually. The light emitted from the sample (resulting from each particular on-state micromirror 42 being modulated) can be correlated to the respective micromirror 42, and the emitted light accurately located within the spatial map of light emitted from the tissue sample. The cross-correlation performed by the analyzer 36 enables the emitted light attributable to the region of the tissue sample interrogated to be extracted and accurately located within the spatial map of silent region light emitted from the tissue sample 38. The pseudorandom noise-like code technique represents one coding technique that can be used for correlation. The present disclosure is not limited to using a pseudorandom noise-like code technique, or any particular coding technique.

As stated above, the number of micromirrors 42 within the DMD 30 that are sequentially disposed in an on-state during the scanning process (and conversely the number of micromirrors 42 disposed in the off-state) can be varied to suit the application at hand. Using a relatively small subset of on-state micromirrors 42 during the sequential scanning process can facilitate the correlation process (e.g., provide a high-speed process), but is not required.

The spatial resolution of the emitted light map can also be varied to suit the application at hand. As stated above, one or more array columns (or one or more rows) may be disposed in an on-state and illuminated with light, which is subsequently directed to the tissue sample. Alternatively, an array region that includes on-state micromirrors 42 within a plurality of columns and rows may be illuminated. In some embodiments, the coordination between the scanner 28 and the DMD may assume a "macro-pixel" arrangement wherein a plurality of micromirrors 42 (e.g., a 2×5 block of pixels from adjoining columns or rows, or a 5×5 block of micromirrors) are controlled in unison (e.g., see FIGS. 6 and 7), and the consequent light emitted from the tissue sample is collectively cross-correlated and entered into the emitted light spatial map. Such an arrangement will provide a lower spatial resolution emitted light spatial map. In some applications, a lower resolution silent region emitted light image will suffice for the application at hand. However, the present disclosure provides the operator with the versatility to satisfy multiple different applications. For example, the present system 18 may be configured to scan a tissue sample 38 at a first lower spatial resolution to ascertain the presence or absence of cancerous tissue. If the presence of cancerous tissue is determined, the present system 18 can be controlled to scan the portion of the tissue sample 38 indicating a presence of cancerous tissue again, the second time at a higher spatial resolution; e.g., where emitted light is attributable to a fewer number of micromirrors 42 (e.g., a single micromirror as described above), and therefore a smaller region of the tissue sample 38 to provide more detailed information regarding the cancerous tissue, including the relative position of the cancerous tissue which may be useful in ascertaining tumor margin position. FIG. 7, for example, diagrammatically illustrates an enlarged view of the micromirror array and the "laser spot" (i.e., the area of the array subject to light from the light source). In some embodiments, the laser spot may encompass "N" number of micromirrors 42. In a low spatial resolution, the micromirrors 42 under the laser spot (and therefore the area of the interrogating light) may be collectively considered collectively (e.g., the "macro-pixel" described above). To increase the spatial resolution, the micromirrors 42 within the laser spot could be considered individually. Alternatively, in some embodiments the area of the laser spot may be increased or decreased and the number of micromirrors 42 in the on-state respectively increased or decreased to alter the resolution.

In some embodiments of the present disclosure system 18, the system may include structure to facilitate registration of the silent region emitted light spatial map with the tissue sample. For example, the system may include an imaging device 44 (e.g., a camera) that provides an actual image of the tissue sample 38 and the analyzer 36 may be configured to overlay or otherwise correlate the image of the tissue sample 38 and the silent region emitted light spatial map. The aforesaid correlation may be useful in visually identifying which specific regions of the tissue sample 38 show evidence of that cancerous cells are present. The present disclosure is not limited to this particular means of registering or locating the silent region emitted light spatial map relative to the tissue sample. For example, the system 18 may include the use of positional markers applied to the tissue sample with known locations that can be sensed by the interrogation process.

It is noted that the system diagrammatically shown in FIG. 5 illustrates a tissue sample disposed in a known location; e.g., an ex-vivo tissue sample 38 disposed on a platen. As described above, the present disclosure can be configured for use in mapping both in-vivo and ex-vivo tissue samples. In a system configured to map in-vivo tissue samples that system may include a probe that can be operated by a clinician at the tissue sample site.

It is further noted that various connections are set forth between elements in the present description and drawings (the contents of which are included in this disclosure by way of reference). It is noted that these connections are general and, unless specified otherwise, may be direct or indirect and that this specification is not intended to be limiting in this respect. A coupling between two or more entities may refer to a direct connection or an indirect connection. An indirect connection may incorporate one or more intervening entities or a space/gap between the entities that are being coupled to one another.

Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

Each of the following references is hereby incorporated by reference in its entirety.

REFERENCES

1. Nguyen and Tsien, "Fluorescence-guided surgery with live molecular navigation—a new cutting edge", Nat Rev Cancer, 13(9), pp. 653-662, 2013.
2. Tummers, et al., "Real-time intraoperative detection of breast cancer using near-infrared fluorescence imaging and methylene blue", Eur J Surg Oncol., 40(7), 850-858, 2014.
3. Dahr et al., "A diffuse reflectance spectral imaging system for tumor margin assessment using custom annular photodiode arrays", Biomedical Optics Express, 3, (12), 2012.
4. Harmsen et al., "Cancer imaging using surface-enhanced resonance Raman scattering nanoparticles", Nat Protoc.; 11(4): 664-87, 2016
5. Matousek et al., "Noninvasive Raman spectroscopy of human tissue in vivo," Appl. Spectrosc. 60(7), 758-763, 2006.
6. Mahadevan-Jansen, Richards-Kortum, "Raman spectroscopy for the detection of cancers and precancers", J Biomed Opt.; 1(1):31-70, 1996.
7. Talari, A. et al., "Raman Spectroscopy of Biological Tissues", Applied Spectroscopy Reviews, 50:1, 46-111, 2015.
8. Pence I., Mahadevan-Jansen A., "Clinical instrumentation and applications of Raman spectroscopy", Chem Soc Rev.; 45 (7):1958-1979, 2016.
9. Yaroslaysky. A, et al., "Delineating nonmelanoma skin cancer margins using terahertz and optical imaging", J of Biomedical Photonics & Eng., 3(1), 2017.
10. Ifa and Eberlin, "Ambient Ionization Mass Spectrometry for Cancer Diagnosis and Surgical Margin Evaluation", Clin Chem.; 62(1), 2016.
11. Zhang et al., "Nondestructive tissue analysis for ex vivo and in vivo cancer diagnosis using a handheld mass spectrometry system", Science Translational Medicine, 9, 2017.
12. Warburg, O., "On the origin of cancer cells", Science 123, pp. 309-314, 1956.
13. Gatenby et al., "Why do cancers have high aerobic glycolysis?", Nature Rev Cancer, 4, 891, 2004

14. Webb et al., "Dysregulated pH: a perfect storm for cancer progression", Nature Reviews. Cancer, 11, p 671, 2011
15. Andreev, et al., "pH-sensitive membrane peptides (pH-LIPs) as a novel class of delivery Agents", Mol. Membr. Biol., 27, pp. 341-352, 2010
16. Adochite et al., "Targeting Breast Tumors with pH (Low) Insertion Peptides", Mol. Pharmaceutics, 11 (8), pp 2896-2905, 2014
17. Werakkoddy et al., "Novel pH-Sensitive Cyclic Peptides", Scientific Reports, 6, 2016.
18. Korzeniowska et al., "Intracellular pH-sensing using core/shell silica nanoparticles", J Biomed Nanotechnol., 10(7), pp. 1336-45, 2014
19. Tsuchikama and An, "Antibody-drug conjugates: recent advances in conjugation and linker chemistries", Protein Cell, 9, pp. 33-46, 2018.
20. Demoin, et al. PET imaging of extracellular pH in tumors with 64Cu- and 18F-labeled pHLIP peptides: A structure-activity optimization study. Bioconjugate Chem. 2016; 27:2014-2023.
21. Wyatt et al., Applications of pHLIP Technology for Cancer Imaging and Therapy, Trends Biotechnol. 2017 July, 35(7): 653-664
22. Antosh M P, et al. Enhancement of radiation effect on cancer cells by gold-pHLIP. Proc Natl Acad Sci USA; 112: pp. 5372-5376, 2015.
23. Yao L, et al. pHLIP peptide targets nanogold particles to tumors. Proc Natl Acad Sci USA; 110:465-470, 2013.
24. Yu et al, "A pH-Driven and photoresponsive nanocarrier: Remotely-controlled by near-infrared light for stepwise antitumor treatment", Biomaterials; 79: pp. 25-35, 2016.
25. "pHLIP (pH Low Insertion peptide) Technology for Cancer Diagnosis and Treatment", Internet article at www.biophys.phys.uri.edu/pHLIP.html, 8/22/19
26. Jamieson et al., "Tracking intracellular uptake and localization of alkyne tagged fatty acids using Raman spectroscopy", Spectrochimica Acta Part A: Molecular and Biomolecular Spectroscopy 197, pp. 30-36 (2018).

What is claimed is:

1. A system for mapping a tissue sample, comprising:
   a light source configured to emit a beam of light;
   a scanner;
   a digital mirror device (DMD) having an orthogonal array of micromirrors, each micromirror selectively controllable to be in an on-state or an off-state;
   at least one light detector; and
   an analyzer in communication with the light source, the scanner, the DMD, the at least one light detector, and a memory storing instructions, which instructions when executed cause the processor to:
      control the light source to produce the beam of light;
      control the scanner to scan the DMD with the beam of light;
      control the DMD to have a subset of micromirrors within the micromirror array in the on-state aligned with the beam of light scanning the DMD, and the micromirrors in the micromirror array not in the subset in the off-state, wherein at least some of the micromirrors within the subset of micromirrors in the on-state direct the beam of light to a tissue sample location;
      assign one or more location codes to the subset of micromirrors in the on-state indicative of a location of the subset of micromirrors within the micromirror array;
      control the at least light detector to receive Raman spectra light emitted from a tissue sample disposed in the tissue sample location, the Raman emitted light produced by the beam of light interrogation of the tissue sample, and to produce signals representative of the emitted light;
      correlate the assigned one or more location codes of the subset of micromirrors with the signals representative of the Raman emitted light produced by at least one light detector; and
      produce a spatial map of the Raman emitted light using the signals representative of the Raman emitted light and the correlation between the assigned one or more location codes of the subset of micromirrors and the signals.

2. The system of claim 1, wherein the light source includes one or more lasers, with each laser configured to emit a beam of light at a wavelength different from the other said lasers, and configured to cause said Raman emitted light to have a wavelength in the Raman silent region when interacting with at least one of an alkyne, nitrile, or azide moiety disposed with the tissue sample.

3. The system of claim 2, wherein the scanner is an X-Y Galvanometer scanner.

4. The system of claim 1, wherein the instructions when executed cause the processor to alter a resolution of the spatial map of the Raman emitted light, including controlling the DMD to increase the number of micromirrors in the subset of micromirrors within the micromirror array, or decreasing the number of micromirrors in the subset of micromirrors within the micromirror array.

5. The system of claim 4, wherein the instructions when executed cause the processor to control the DMD to increase the number of micromirrors in the subset of micromirrors within the micromirror array, and to cause the scanner to perform a first scan of the DMD at a lower said resolution, and to subsequently control the DMD to decrease the number of micromirrors in the subset of micromirrors within the micromirror array, and to cause the scanner to perform a second scan of at least a portion of the DMD at a higher said resolution.

6. The system of claim 1, wherein the system further comprises one or more narrow bandpass filters, the one or more narrow bandpass filters disposed to receive the emitted light prior to the emitted light being received by the at least one light detector, and the one or more narrow bandpass filters configured to only pass wavelengths of said Raman emitted light in a Raman silent region.

7. The system of claim 6, wherein the signals produced by the at least one light detector are representative of the Raman emitted light wavelengths in the Raman silent region.

8. The system of claim 7, wherein the spatial map of the Raman emitted light represents Raman emitted light wavelengths in the Raman silent region.

9. The system of claim 1, wherein the one or more assigned location codes are a pseudorandom noise-like code.

10. The system of claim 1, wherein the light source is a laser that selectively produces a laser beam, and wherein the system further comprises a line generating lens configured to convert the laser beam to a laser line having a width and a length, with the length extending a distance substantially greater than the width.

11. A method of mapping a tissue sample, comprising:
    providing a system having a light source configured to emit a beam of light, a scanner, a digital mirror device (DMD) having an orthogonal array of micromirrors, each micromirror selectively controllable to be in an on-state or an off-state, at least one light detector, and an analyzer in communication with the light source, the scanner, the DMD, and the at least one light detector;

providing a tissue sample inoculated with a material containing pHLIPs conjugated with one or more Raman reporters (RR);

scanning the DMD with a light beam produced by the light source, the scanning including using the scanner to move the light beam relative to the DMD;

controlling the DMD to have a subset of micromirrors within the micromirror array in the on-state aligned with the light beam scanning the DMD, and the micromirrors in the micromirror array not in the subset in the off-state, wherein at least some of the micromirrors in the subset of micromirrors in the on-state are configured to direct the light beam to interrogate the tissue sample, wherein the interrogation produces Raman emitted light from the tissue sample;

assigning one or more location codes to the subset of micromirrors in the on-state indicative of a location of the subset of micromirrors within the micromirror array;

receiving the Raman emitted light from the tissue sample using the at least one light detector, and producing signals representative of the Raman emitted light;

correlating the assigned one or more location codes of the subset of micromirrors with the signals representative of the Raman emitted light; and producing a spatial map of the Raman emitted light using the signals representative of the Raman emitted light and the correlation between the assigned one or more location codes of the subset of micromirrors and the signals.

12. The method of claim 11, wherein the Raman reporters are configured to produce a Raman spectrum in a Raman silent region when interrogated by the light beam.

13. The method of claim 12, wherein the system further comprises one or more narrow bandpass filters, the one or more narrow bandpass filters disposed to receive the Raman emitted light prior to the Raman emitted light being received by the at least one light detector, and the one or more narrow bandpass filters configured to only pass wavelengths of said Raman emitted light in a Raman silent region.

14. The method of claim 12, wherein the Raman reporters are configured with at least one of an alkyne, nitrile, or azide moiety.

15. The method of claim 11, further comprising filtering the Raman emitted light prior to the Raman emitted light being received by the at least one light detector, the filtering allowing only wavelengths of the Raman emitted light in a Raman silent region to pass through to the at least one detector.

16. The method of claim 15, wherein the spatial map of the Raman emitted light represents emitted light wavelengths in the Raman silent region.

17. The method of claim 11, wherein the controlling of the DMD includes selecting a resolution of the spatial map of the Raman emitted light, the subset of micromirrors within the micromirror array having a number of micromirrors, and the resolution based in part on the number of micromirrors within the subset of micromirrors.

18. The method of claim 17, further comprising scanning the DMD a first time to produce the spatial map of Raman emitted light at a first said resolution, and scanning at least a portion of the DMD a second time to produce the spatial map of Raman emitted light at a second said resolution, which second said resolution is greater than the first said resolution.

19. The method of claim 11, wherein the step of assigning said one or more location codes to the subset of micromirrors in the on-state includes assigning a pseudorandom noise-like code.

20. The method of claim 19, wherein the line generating lens is configured to produce the laser beam line in an orientation that aligns with rows in the orthogonal array of micromirrors, or in an orientation that aligns with columns in the orthogonal array of micromirrors.

21. The method of claim 11, wherein the light source is a laser that selectively produces a laser beam, and further comprising converting the laser beam to a laser beam line having a width and a length, with the length extending a distance substantially greater than the width, using a line generating lens.

* * * * *